United States Patent [19]  [11]  4,346,482
Tennant et al.  [45]  Aug. 31, 1982

[54] LIVING CONTACT LENS

[76] Inventors: Jerald L. Tennant, 806 Greentree La.; Heinz J. Smirmaul, 1207 Spring Lake Dr., both of Duncanville, Tex. 75116

[21] Appl. No.: 227,255

[22] Filed: Jan. 22, 1981

[51] Int. Cl.³ .......................... A61F 1/16; A61F 1/24
[52] U.S. Cl. ......................................... 3/13; 128/1 R; 128/305; 351/160 R
[58] Field of Search ................. 3/13, 1; 128/1 R, 305; 351/160 R

[56] References Cited

U.S. PATENT DOCUMENTS 4,126,904  11/1978  Shepard .................................. 3/13

OTHER PUBLICATIONS

Friedlander, M. H., et al., "Keratophakia Using Preserved Lenticules", *Ophthalmology* Jul. 1980, vol. 87, No. 7 pp. 687–692.

"Living Contact Lens May Aid Aphakic Patients", *Ophthalmology Times*, Aug. 1980.
"Medicine-Shaping Up the Blurry Eye", *Time*, Sep. 22, 1980, p. 51.
Boyd, Benjamin, F. Highlights of Ophthalmology, vol. VIII, No. 6, Panamerican Congress of Ophthalmology, Acapulco, Mexico, May 10-15, 1981, pp. 1–6.

*Primary Examiner*—Ronald L. Frinks
*Attorney, Agent, or Firm*—Richards, Harris & Medlock

[57] ABSTRACT

A contact lens (14) for insertion into the cornea (20) of a patient is provided. The contact lens (14) includes a circular portion of a donor cornea (10) anteriorly curved for correction of the patient's vision. The contact lens (14) is posteriorly ground (16) to correspond to the curvature of the patient's eye. The posterior portion (16) of the lens (14) includes a depending axially posteriorly directed integral ring (18) for insertion into and retention by the patient's cornea (20).

2 Claims, 6 Drawing Figures

LIVING CONTACT LENS

TECHNICAL FIELD

This invention relates to contact lenses, and more particularly to a living contact lens with improved corneal fixation.

BACKGROUND ART

The process by which one visually perceives involves light entering the eye in parallel rays, which are generally bent as they pass through the cornea and lens of the eye. In the normal eye, these light rays converge, or focus, on the retina at the back of the eyeball. Electrical impulses then transmit a sharp image to the brain.

Two common vision problems nearsighted (myopia) and farsighted (hyperopia) involve improper shaped eyeballs. In the nearsighted vision problem, the eyeball is usually too long or the cornea too curved, so that the light rays entering the eye come to a focal point in front of the retina. In the farsighted vision problem, the eyeball is too short or the cornea too flat and the light rays, if they could pass through the eyeball, would converge behind the retina. Eyeglasses and contact lenses change the focal point of the light entering the eye to provide corrected vision for near and farsighted vision problems.

Another approach to correct nearsightedness and farsightedness is to change the curvature of the cornea so that images fall directly on the retina. A corneal operation termed refractive keratoplasty has been used by Dr. Jose' I. Barraquer of Bogota, Columbia. In one of Dr. Barraquer's procedures known as keratomileusis (corneal carving) the front of the cornea is sliced off. The sliced off cornea is then frozen and reshaped on its interior surface by a cryolathe. After thawing, the cornea slice is stitched back on the eye. To correct nearsightedness, under Dr. Barraquer's process, the surgeon removes tissue from the center of the cornea, thereby flattening it. In farsighted patients, tissue is removed from the periphery of the cornea to accentuate the curve. A similar operation, called keratophakia (cornea lens) is used to correct only farsightedness. In this operation, after the front of the cornea is sliced off, a reshaped donor cornea is placed on the remaining cornea. The front of the original patient's cornea is then resewn, resulting in a more sharply curved corneal structure.

An additional surgical procedure in which a donor cornea is ground and sewn onto a recepient cornea has been proposed by Dr. Herbert E. Kaufman of New Orleans. In this procedure, the epithelial layer of the cornea is removed. A cut, approximately 0.1 to 0.3 millimeters in length, is made at the periphery of the cornea, and the donor contact lens or "button" is sewn on. The donor contact lens is frozen prior to being ground and therefore has no epithelium layer and virtually no living keratocytes. The keratocytes are repopulated in the collagen of the donor contact lens from the host cornea.

In contrast to the procedure of Dr. Barraquer, the procedure of Dr. Kaufman does not remove a piece of the cornea, but only the epithelial layer of the cornea is removed with the Bowman membrane left intact. Dr. Kaufman's procedure also makes it possible for the donor cornea to be ground to the needs of a particular patient in advance of surgery. It would not be necessary therefore for the piece of cornea removed from the patient's eye or a donor eye to be ground on a lathe during the operation.

The above procedures developed by Dr. Barraquer and Dr. Kaufman involve sophisticated and somewhat complex lathing equipment and mathematical analysis. It has been proposed that precut lenticules or lamellar discs could be stored based upon predetermined dioptric correction of a patient. The ophthalmic surgeon would then, based upon a calculated preoperative dioptric correction, obtain a donor cornea previously ground to the determined correction needed by his patient. Lamellar dissection and suturing of the donor cornea would then be performed to complete the surgical operation using the living contact lenses. Lenticule preservation is discussed in an article by M. H. Friedlander entitled "Keratophakia Using Preserved Lenticules", Ophthalmology, July 1980, Volume 87, No. 7.

With the development of surgical procedures for changng the shape of the cornea to correct for myopia and hyperopia and improved lenticule preservation techniques, a need for refined surgical procedures for performing refractory keratoplasty has arisen. Particularly, a need has arisen for surgical techniques and lenticule structures fitted to the patient's cornea that ensure that the lenticule is retained by the patient's cornea. A need has thus arisen for a lenticule for use in refractive keratoplasty surgical operations that can be easily handled in a standard operating room and which has improved corneal fixation.

DISCLOSURE OF THE INVENTION

In accordance with the present invention, a living contact lens for insertion into the cornea of a patient is provided to simplify and make more reliable refractive keratoplasty surgical operations.

In accordance with the present invention, a contact lens for insertion into the cornea of a patient is provided. The lens includes a circular portion of a donor cornea anteriorly curved for correction of the patient's vision. The circular portion posterior surface is ground to correspond to the curvature of the patient's eye.

In accordance with another aspect of the present invention, a contact lens for insertion into the cornea of a patient is provided. The lens includes a circular portion of a donor cornea anteriorly curved for correction of the patient's vision. The circular portion posterior surface is ground to correspond to the curvature of the patient's eye and includes a depending axial posteriorly directed integral ring of height less than the thickness of the patient's cornea for insertion into and retention by the patient's cornea.

BRIEF DESCRIPTION OF THE DRAWINGS

For a more complete understanding of the present invention and for further advantages thereof, reference is now made to the following Detailed Description taken in conjunction with the accompanying Drawings, in which.

DETAILED DESCRIPTION

Figure 1:
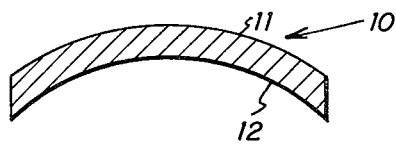
FIG. 1 is a cross-sectional view of a precut lenticule.

FIG. 1 illustrates a precut lenticule, generally identified by the numeral 10. Lenticule 10 may be obtained from the cornea of a human or other mammals such as, for example, cattle and pigs. Preservation techniques well known to those skilled in the art, are used to preserve lenticule 10 as needed for surgical insertion into the cornea of a patient.

Anterior surface 11 of lenticule 10 is molded in a fixture on a cryolathe and frozen. The curvature which anterior surface 11 assumes is dictated by the fixture which is designed according to computer calculations for the desired dioptric correction needed by the patient. Once lenticule 10 is frozen, posterior surface 12 of lenticule 10 is lathed according to the present invention to correspond to the curvature of the patient's eye. Posterior surface 12 is ground using a cryolathe and techniques well known to those skilled in the art. An important aspect of the present invention is the grinding of posterior surface 12 of lenticule 10 to match the curvature of the patient's eye. This matching ensures that the anterior curvature of lenticule 10 does not change when lenticule 10 is inserted into the patient's eye, unlike previously suggested techniques which have resulted in poorly corrected vision due to changes in the anterior curvature after insertion.

Lenticule 10 prior to lathing is frozen using techniques well known to those skilled in the art. The freezing process kills the keratocytes present in the lenticule, such that only the collagen remains for fixation to the cornea of the patient.

Figure 2:
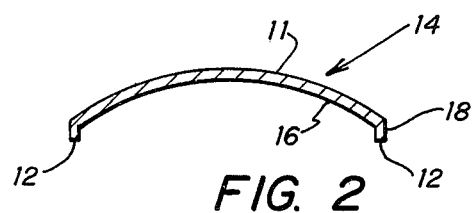
FIG. 2 is a cross-sectional view of a lenticule ground according to the present invention.

FIG. 2 illustrates lenticule 14 of the present invention which results from the lathing of lenticule 10 (FIG. 1). Only a portion of posterior surface 12 remains in lenticule 14 and a new posterior surface 16 represents the portion of lenticule 14 that has been ground. Depending from posterior surface 16 and terminating at posterior surface 12 of lenticule 14 is an integral ring 18 which is axially posteriorly directed from posterior surface 16. Ring 18 may be approximately, for example, 0.1–0.2 millimeters in thickness. An important aspect of the present invention is the use of ring 18 for affixing lenticule 14 into the cornea of a patient's eye.

Figure 3:
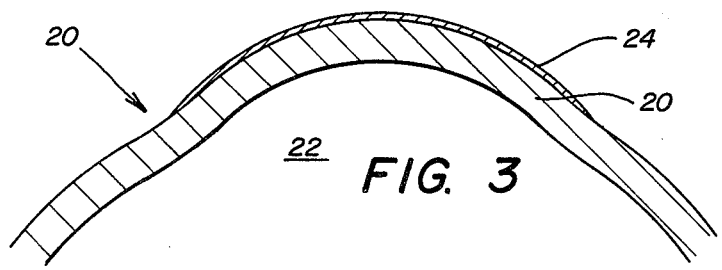
FIG. 3 is a cross-sectional view of a cornea.

FIG. 3 illustrates a simplified cross-sectional view of a cornea 20 of an eye 22 to undergo a refractive keratoplasty surgical operation. Cornea 20 includes epithelial layer 24.

Figure 4:
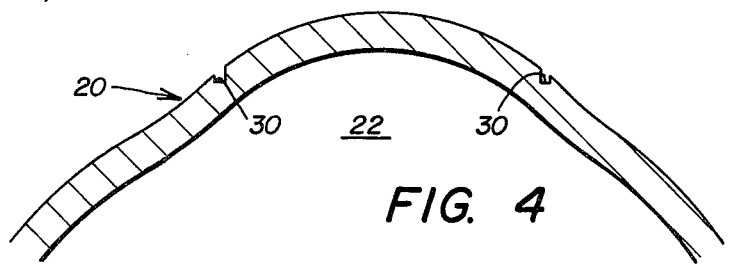
FIG. 4 is a cross-sectional view of a cornea with the epithelial layer removed and prepared to receive the lenticule of the present invention.

FIG. 4 illustrates eye 22 with epithelial layer 24 removed. A circular groove 30 is formed in cornea 20 and has a thickness of approximately 0.1 to 0.2 millimeters. Groove 30 can be formed using a corneal trephine having axial blades for performing an axial cut into cornea 20. Such a trephine is described in copending U.S. patent application Ser. No. 06/175,577, filed on Aug. 5, 1980 and entitled "Corneal Trephine".

Figure 5:
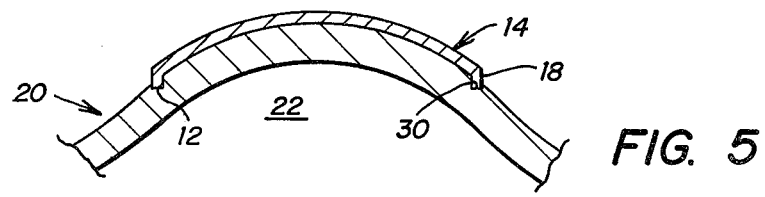
FIG. 5 is a cross-sectional view of a cornea with the lenticule of FIG. 2 inserted into the cornea of a patient's eye.
Figure 6:
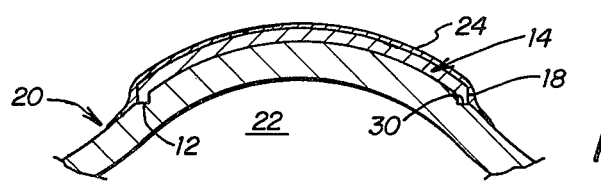
FIG. 6 is a cross-sectional view of the cornea of FIG. 5 and a newly grown epithelial layer.

Referring now to FIG. 5, lenticule 14 of the present invention has been inserted into cornea 20 of the patient such that ring 18 is positioned within groove 30 for positive fixation to cornea 20. It therefore can be seen that the use of ring 18 and groove 30 form physical structure for positively receiving and affixing lenticule 14 to cornea 20 in the refractive keratoplasty operation. Ring 18 may then be sutured to cornea 20 for temporary affixation until normal scarring takes place between cornea 20 and ring 18 of lenticule 14.

It therefore can be seen that the present lenticule having a depending posteriorly disposed ring provides for positive fixation of a lenticule into the cornea of a patient's eye in refractive keratoplasty surgery. Furthermore, the present invention ensures matching of the posterior surface of the donor cornea to the curvature of the patient's eye, such that the curvature of the anterior surface of the donor cornea does not change after insertion into the eye of the patient.

Whereas the present invention has been described with respect to specific embodiments thereof, it will be understood that various changes and modifications will be suggested to one skilled in the art and it is intended to encompass such changes and modifications as fall within the scope of the appended claims.

We claim:

1. A contact lens for insertion into the cornea of a patient comprising:

a circular portion of a donor cornea having an anterior surface and a posterior surface, said anterior surface being curved for correction of the patient's vision;

said circular portion posterior surface being ground to correspond to the curvature of the patient's eye; and said circular portion having a depending axially posteriorly directed ring, said ring being integral with said posterior surface of said circular portion and having a height less than the thickness of the patient's cornea for insertion into and retention by the patient's cornea.

2. A method for performing refractive keratoplasty on a patient's eye comprising the steps of:

molding the anterior surface of a donor cornea for correction of the patient's vision;

grinding the posterior surface of a donor cornea to correspond to the curvature of the patient's eye;

grinding an axially posteriorly directed integral ring into the posterior surface of the donor cornea;

removing the epithelial layer of the cornea of the patient's eye;

cutting a groove in the patient's cornea for receiving the ring; and inserting the ring of the donor cornea into the groove of the patient's cornea for positively affixing the donor cornea into the patient's cornea.

* * * * *